United States Patent [19]

Kitayama

[11] Patent Number: 5,435,006

[45] Date of Patent: Jul. 25, 1995

[54] EYE MASK

[76] Inventor: Hidehiro Kitayama, 2-22-11 Yanagibashi Taito-Ku, Tokyo, Japan

[21] Appl. No.: 319,274

[22] Filed: Oct. 6, 1994

Related U.S. Application Data

[63] Continuation of Ser. No. 164,212, Dec. 8, 1993, abandoned.

[51] Int. Cl.6 ............................................... A61F 9/04
[52] U.S. Cl. ............................................. 2/15; 2/433
[58] Field of Search ...................... 2/15, 433, 426, 439, 2/431, 447; 128/858

[56] References Cited

U.S. PATENT DOCUMENTS

| 2,305,080 | 12/1942 | Hemphill et al. | 2/15 |
| 2,946,133 | 7/1960 | Williams | 2/15 X |
| 4,872,217 | 10/1989 | Kitayama | 2/15 |

FOREIGN PATENT DOCUMENTS 0866887  6/1941  France ..................................... 2/433

Primary Examiner—Peter Nerbun
Attorney, Agent, or Firm—Cislo & Thomas

[57] ABSTRACT

An eye mask is provided having a main portion formed of a soft sheet material and a back contact member mounted to a back face of a main portion. A free end portion of the back contact member circumscribes the perimeter of the main portion and extends inwardly to overlie a portion of the rear surface of the main portion to improve the fit and comfort of the eye mask.

1 Claim, 2 Drawing Sheets

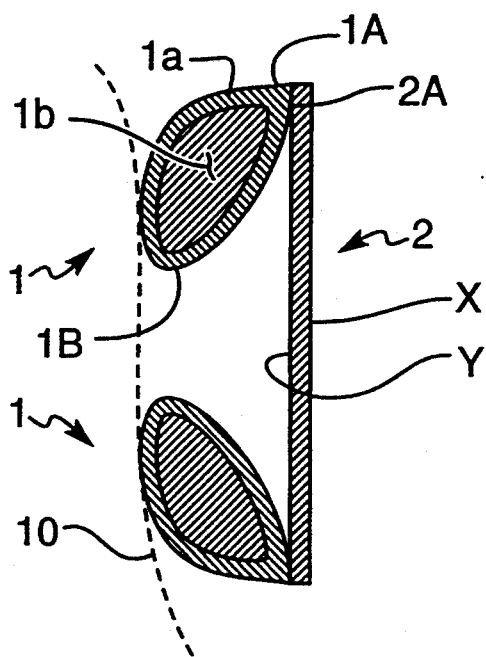
Fig. 3  (section A – A of Fig. 2)
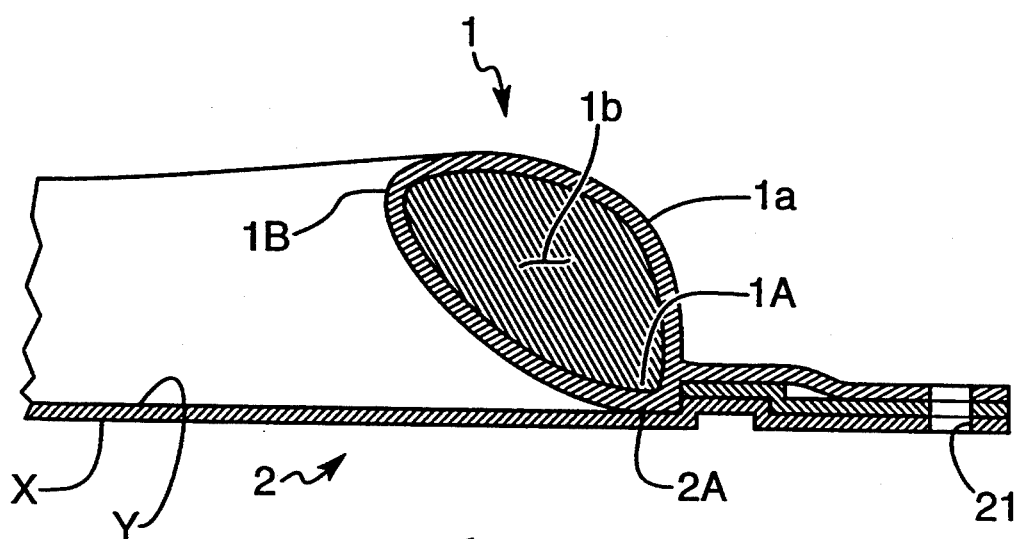
Fig. 4  (section B – B of Fig. 2)

EYE MASK

This is a continuation of application Ser. No. 08/164,212 filed Dec. 8, 1993, now abandoned.

FIELD OF THE INVENTION

This invention relates to an eye mask and, more particularly, relates to a novel improvement of the contact characteristics of the mask with a user's face. The contact characteristics are improved by having a free end portion of a back contact member which contacts a user's face.

BACKGROUND OF THE INVENTION

Conventionally, an eye mask is used as shown in FIG. 1 (this is shown in Japanese laid open Utility Patent No. 61-34221 and No. 3422/1986). A back contact member 1 is fully mounted to a main portion 2. For example, the back contact member 1 is formed by an injection formation.

Since the conventional articles are constructed as just described, there have been the following problems.

Specifically, the softness of said back contact member 1 is a problem, as its softness is limited when an eye mask is mounted to a user's face, because said back contact member 1 is connected to a main portion 2 as one integral body. Therefore, it is very difficult to fit the eye mask to the different facial contours of different users. A person may develop a pain in his face after wearing such a mask for a long time, for example, when used by a foreign traveler.

SUMMARY OF THE INVENTION

To solve the above-described problems, it is an object of the present invention to provide an eye mask in which an inner portion of a back contact member is formed as a free end portion, whereby contact characteristics with a face are remarkably improved.

Accordingly, an eye mask is provided comprising in combination:

a main portion formed by a soft sheet material having an eye portion of a plurality of small holes formed therethrough. A back contact member formed of soft material mounted to the back face of the main portion. A free end portion of the back contact member is formed by affixing only one end of the contact member to the main portion.

In particular, the back contact member is formed with a ring shaped cross-sectional contour.

BRIEF DESCRIPTION OF THE DRAWINGS

FIG. 3 is an enlarged cross-sectional view taken along the section line A—A of FIG. 2; and FIG. 4 is an enlarged cross-sectional view taken along the section line. B—B of FIG. 2.

DESCRIPTION OF THE PREFERRED EMBODIMENT

A description will now be given by way of the accompanying drawings with respect to the eye mask according to the present invention.

Figure 2:
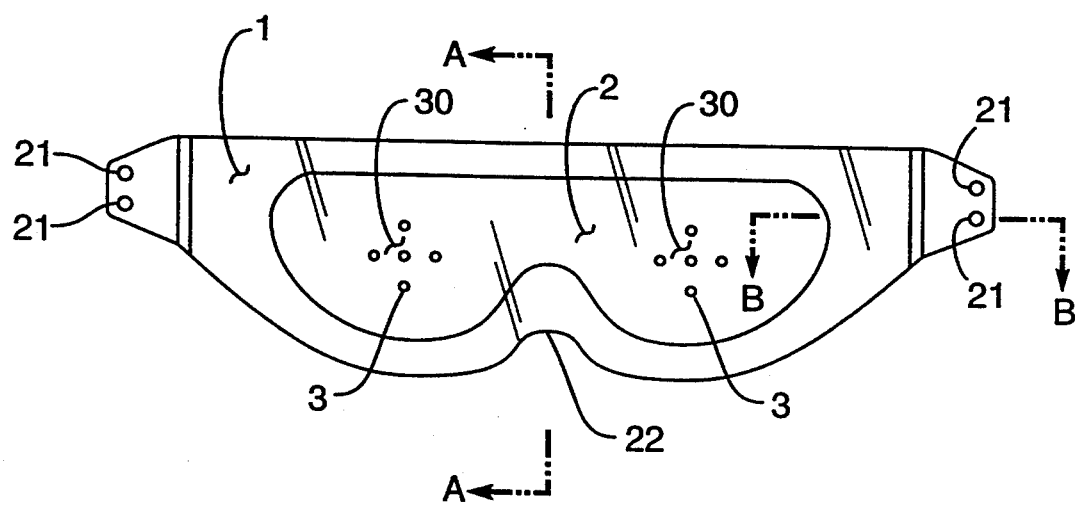
FIG. 2 is a plan view of the back of the eye mask of the present invention.

Referring to FIGS. 2 and 4, a back contact member 1 is formed by a soft sheet material and is mounted to a main portion 2. Back contact member 1 extends completely about the periphery of main portion 2. The main portion 2 has a pair of portions 30, each with a plurality of small holes 3 formed therethrough. A recess portion 22 is provided for contact with a user's nose. The back contact member 1 is composed of an outer skin 1a having a ring or bag cross-sectional shape, and a soft material 1b mounted in the outer skin 1a. The eye portion 30 is used for seeing through the mask.

An outer end portion 1A of the back contact member 1 is mounted to a back outer portion 2A of the main portion 2. An inwardly directed portion of the back contact member 1 overlies a portion of the main portion 2, having a free end portion 1B which is not connected to the main portion 2.

Figure 1:
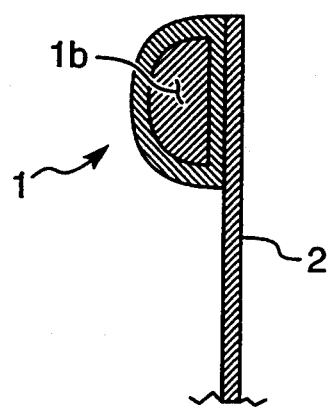
FIG. 1 is a cross-sectional view of prior art eye mask.

Therefore, the free end portion 1B is constructed to provide a floating condition with respect to the main portion, and is different from the conventional construction shown in FIG. 1. The free end portion of the back contact member provides elasticity when the eye mask is mounted to a user's face 10, providing a peripheral padded portion circumscribing the nose recess 22 and eye portions 30 of the main portion 2. The fit of the mask and the contact characteristics are remarkably improved.

A connection between the back contact member 1 and main portion 2 is constructed in one-piece formation, where the two components are heat sealed together, as described.

Further, a pair of holes 21 is formed on each of the two end portions of the main portion 2. The eye mask is mounted to a user's face by a cord (not shown), which is connected to the holes 21.

In FIGS. 3 and 4, "X" indicates a front surface of the eye mask and "Y" indicates a back surface of the eye mask.

According to the present invention, an elasticity of back contact member is remarkably improved and the fit and contact characteristics are improved. A user is thereby able to use the eye mask for long time periods without fatigue.

What is claimed is:

1. An eye mask comprising in combination:
a front portion fabricated of soft, pliable material and configured to overlie the eyes of a wearer, each eye portion having a plurality of spaced apertures therein, said front portion having an outer surface, an opposing inner surface, and a recess formed in a perimeter thereof to accommodate a wearer's nose;
a back portion having an outer perimeter congruently configured to said front portion perimeter and only perimetrically secured thereto on said inner surface, said back portion having an unsecured padded portion extending (1) circumferentially about said perimeter of said front portion and circumscribing the nose and eyes of the wearer to form a circumscribed portion of said inner surface, and (2) inwardly to overlie said circumscribed portion of said inner surface of said front portion, whereby said eye mask is comfortably worn by the wearer; and attachment means secured to opposing ends of said eye mask for attaching said eye mask to the head of the wearer.

* * * * *